(12) United States Patent
Rousu et al.

(10) Patent No.: US 12,220,218 B2
(45) Date of Patent: Feb. 11, 2025

(54) CATHETER CONTACT FORCE SENSOR

(71) Applicant: Biosense Webster (Israel) Ltd., Yokneam (IL)

(72) Inventors: Corey M. Rousu, Huntington Beach, CA (US); Matthew W. Hitzeroth, Irwindale, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 18/536,517

(22) Filed: Dec. 12, 2023

(65) Prior Publication Data
US 2024/0099605 A1 Mar. 28, 2024

Related U.S. Application Data

(63) Continuation of application No. 16/953,578, filed on Nov. 20, 2020, now Pat. No. 11,872,026.
(Continued)

(51) Int. Cl.
*A61B 5/00* (2006.01)
*A61B 5/06* (2006.01)
(Continued)

(52) U.S. Cl.
CPC ............ *A61B 5/061* (2013.01); *A61B 5/6852* (2013.01); *A61M 25/005* (2013.01);
(Continued)

(58) Field of Classification Search
CPC ...... A61B 18/1492; A61B 2018/00172; A61B 2018/00178; A61B 2018/00196;
(Continued)

(56) References Cited

U.S. PATENT DOCUMENTS 5,053,747 A  10/1991 Slate et al.
5,099,845 A   3/1992 Besz et al.
(Continued)

FOREIGN PATENT DOCUMENTS

CN  208611483 U  3/2019
JP  H06329996 A  5/1993
(Continued)

OTHER PUBLICATIONS

Extended European Search Report dated Dec. 3, 2020, from corresponding EP Application No. 20188421.0.
(Continued)

*Primary Examiner* — Khadijeh A Vahdat

(57) ABSTRACT

A spring assembly usable with an intravascular catheter can include a tubular body, two mounting surfaces, and a compressible framework. The tubular body extends along a longitudinal axis and is sized to traverse vasculature. Each mounting surface can be configured to engage a substantially planar electrical circuit and is positioned in the tubular body each in a respective plane perpendicular to the longitudinal axis. The mounting surfaces face toward each other in opposite directions. The compressible framework extends between the first and second mounting surfaces. The spring assembly can further include a pair of electrical circuits mounted to the pair mounting surfaces. Each electrical circuit can include an inductive coil such that the pair of electrical circuits is a distance transducer. A change in distance between the pair of electrical circuits can be detected when the compressible framework is compressed and/or bent.

17 Claims, 11 Drawing Sheets

Related U.S. Application Data

(60) Provisional application No. 62/943,572, filed on Dec. 4, 2019.

(51) Int. Cl.
  *A61M 25/00* (2006.01)
  *A61M 25/01* (2006.01)

(52) U.S. Cl.
  CPC .... *A61M 25/0068* (2013.01); *A61M 25/0158* (2013.01); *A61M 2025/0059* (2013.01)

(58) Field of Classification Search
  CPC  A61B 2018/00351; A61B 2018/00577; A61B 2018/00791; A61B 2090/064; A61B 2090/065; A61B 2218/002; A61M 25/005; A61M 25/0068; A61M 25/0158
  See application file for complete search history.

(56) References Cited

U.S. PATENT DOCUMENTS

| | | | |
|---|---|---|---|
| 5,447,529 | A | 9/1995 | Marchlinski et al. |
| 5,836,990 | A | 11/1998 | Li |
| 5,935,079 | A | 8/1999 | Swanson et al. |
| 6,241,724 | B1 | 6/2001 | Fleischman et al. |
| 6,695,808 | B2 | 2/2004 | Tom |
| 6,757,557 | B1 | 6/2004 | Bladen et al. |
| 6,814,733 | B2 | 11/2004 | Schwartz et al. |
| 6,915,149 | B2 | 7/2005 | Ben-Haim |
| 6,997,924 | B2 | 2/2006 | Schwartz et al. |
| 7,156,816 | B2 | 1/2007 | Schwartz et al. |
| 7,536,218 | B2 | 5/2009 | Govari et al. |
| 7,756,576 | B2 | 7/2010 | Levin |
| 9,168,004 | B2 | 10/2015 | Gliner et al. |
| 2005/0203597 | A1 | 9/2005 | Yamazuki et al. |
| 2007/0100332 | A1 | 5/2007 | Paul et al. |
| 2008/0098798 | A1 | 5/2008 | Riley et al. |
| 2009/0093806 | A1 | 4/2009 | Govari et al. |
| 2014/0005661 | A1 | 1/2014 | Shelton, IV et al. |
| 2014/0243821 | A1 | 8/2014 | Salahieh et al. |
| 2017/0055873 | A1 | 3/2017 | Clark et al. |
| 2017/0354467 | A1 | 12/2017 | Rankin et al. |
| 2018/0256110 | A1 | 9/2018 | Govari et al. |
| 2019/0054276 | A1 | 2/2019 | Werneth et al. |

FOREIGN PATENT DOCUMENTS

| | | |
|---|---|---|
| JP | 2018143772 A | 9/2018 |
| WO | 9605768 A1 | 2/1996 |
| WO | 2017087923 A1 | 5/2017 |
| WO | 2019089303 A2 | 5/2019 |

OTHER PUBLICATIONS

Internatinal Search Report and Written Opinion dated Mar. 12, 2021, from Corresponding PCT Application No. PCT/US2020/070838.

Internatinal Preliminary Report on Patentability dated May 17, 2022, from Corresponding PCT Application No. PCT/US2020/070838.

English translation of Search Report dated Apr. 26, 2024, from corresponding Japanese Application No. 2022-533527.

English translation of Notice of Reasons for Refusal dated Apr. 30, 2024, from corresponding Japanese Application No. 2022-533527.

English translation of Written Opinion dated Jul. 8, 2024, from corresponding Japanese Application No. 2022-533527.

English translation of Decision to Grant a Patent dated Aug. 27, 2024, from corresponding Japanese Application No. 2022-533527.

CATHETER CONTACT FORCE SENSOR

CROSS REFERENCE TO RELATED APPLICATIONS

This application is a continuation of U.S. Non-Provisional patent application Ser. No. 16/953,578 filed Nov. 20, 2020, now U.S. Pat. No. 11,872,026, which claims the benefit of priority under the Paris Convention as well as 35 U.S.C. §§ 119 and 120 to prior filed U.S. Provisional Patent Application No. 62/943,572 filed on Dec. 4, 2019, each of which are hereby incorporated by reference as set forth in full herein.

FIELD

The present disclosure relates to instruments for diagnostic and surgical purposes that measure force, pressure, mechanical tension, and/or mechanical compression, and more particularly to catheter-based probes for diagnostic and/or surgical procedures in the heart.

BACKGROUND

Cardia arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to block or modify the propagation of unwanted electrical signals from one portion of the heart to another. The ablation process destroys the unwanted electrical pathways by formation of non-conducting lesions.

Various attempts in the art to verify electrode contact with the tissue have been attempted or suggested including utilizing one more pressure transducers (U.S. Pat. Nos. 6,695,808 and 6,241,724), utilizing an electrode to measure electrical activity in the heart (U.S. Pat. No. 6,915,149), utilizing an electromechanical movement sensor (U.S. Patent Application Publication 2007/0100332), measuring impedance between a tip electrode and a return electrode (U.S. Pat. Nos. 5,935,079, 5,836,990, and 5,447,529), and utilizing fluoroscopic imaging (U.S. Patent Publication 2005/0203597).

U.S. Patent Application Publication No. 2009/0093806 to Govari et al., which is hereby incorporated by reference in its entirety into this application as if set forth in full and attached in the appendix to priority U.S. application 62/943,572, describes another application of contact pressure measurement, in which deformation in response to pressure on a resilient member located at the distal end of a catheter is measured using a sensor.

U.S. Pat. No. 9,168,004 to Gliner, et al., which is hereby incorporated by reference in its entirety into this application as if set forth in full and attached in the appendix to priority U.S. application 62/943,572, describes using machine learning based on impedance between two electrodes to determine catheter electrode contact.

U.S. Patent Publication 2018/0256110 to Govari et al., which is hereby incorporated by reference in its entirety into this application as if set forth in full and attached in the appendix to priority U.S. application 62/943,572, describes a flexible probe having a pair of spring coils and a transducer having a transmitter circuit and a receiver circuit situated on either side of the spring coils. The spring coils deform in response to pressure exerted to the distal tip of the probe to cause the transmitter and receiver circuits to move in relation to each other.

SUMMARY

There is provided, in accordance with some embodiments of the present disclosure a spring assembly usable with an intravascular catheter. The spring assembly can include a tubular body, a first mounting surface configured to engage a substantially planar electrical circuit, a second mounting surface configured to engage a substantially planar electrical circuit, and a compressible framework extending between the first and second mounting surfaces. The tubular body extends along a longitudinal axis. The tubular body is sized to traverse vasculature. The first mounting surface is positioned in the tubular body, perpendicular to the longitudinal axis, and facing a first direction parallel to the longitudinal axis. The second mounting surface is positioned in the tubular body, perpendicular to the longitudinal axis, and facing toward the first mounting surface in a second direction opposite the first direction.

In some embodiments, the spring assembly further includes a first opening in the tubular body and a second opening in the tubular body. The first opening is circumscribed by the first mounting surface and the compressible framework. The second opening is circumscribed by the second mounting surface and the compressible framework. The first and second openings can be at least partially collapsible in response to compression of the compressible framework.

In some embodiments, the spring assembly further includes one or more openings circumscribed by the compressible framework. The one or more openings circumscribed by the compressible framework can be at least partially collapsible in response to compression of the compressible framework.

In some embodiments, the spring assembly further includes third, fourth, fifth, and sixth mounting surfaces each respectively configured to engage a substantially planar electrical circuit and positioned in the tubular body. The first, third, and fifth mounting surfaces are coplanar in a first plane perpendicular to the longitudinal axis. The second, fourth, and sixth mounting surfaces are coplanar in a second plane perpendicular to the longitudinal axis. The third and fourth mounting surfaces are facing toward each other. The fifth and sixth mounting surfaces are facing toward each other.

In some embodiments, the spring assembly includes first, second, third, fourth, and fifth openings. The first opening in the tubular body is circumscribed by the first mounting surface and the compressible framework. The second opening in the tubular body is circumscribed by the second mounting surface and the compressible framework. The third opening in the tubular body is circumscribed by the third mounting surface and the compressible framework. The fourth opening in the tubular body is circumscribed by the fourth mounting surface and the compressible framework. The fifth opening in the tubular body is circumscribed by the fifth mounting surface and the compressible framework. The sixth opening in the tubular body is circumscribed by the sixth mounting surface and the compressible framework. The spring assembly can further include three additional openings each respectively circumscribed by the compressible framework.

In some embodiments including the first, second, third, fourth, fifth, and sixth mounting surfaces, each mounting surface has substantially similar dimensions to each of the remaining mounting surfaces.

In some embodiments including the first, third, and fifth mounting surfaces, the first, third, and fifth mounting surfaces are spaced 120° from each other as measured rotationally in about the longitudinal axis.

In some embodiments including the second, fourth, and sixth mounting surfaces, the second, fourth, and sixth mounting surfaces are spaced 120° from each other as measured rotationally about the longitudinal axis.

In some embodiments, the first mounting surface includes a plurality of T-shaped indentations thereon, and/or the second mounting surface includes a plurality of T-shaped indentations thereon. Some or all of the mounting surfaces include a plurality of T-shaped indentations thereon.

In some embodiments, the spring assembly further includes multiple engagement extensions extending in the first direction from a first end of the tubular body and multiple engagement extensions extending in the second direction from a second end of the tubular body. Each engagement extension on either side of the tubular body includes a protrusion extending therefrom in a circumferential direction about the longitudinal axis.

In some embodiments including multiple engagement extensions, the spring assembly includes exactly three engagement extensions extending in the first direction from the first end of the tubular body and exactly three engagement extensions extending in the second direction from the second end of the tubular body.

In some embodiments, the spring assembly further includes a first electrical circuit and a second electrical circuit. The first electrical circuit is affixed to the first mounting surface. The first electrical circuit includes a first inductive coil. The second electrical circuit is affixed to the second mounting surface. The second electrical circuit includes a second inductive coil.

In some embodiments including the first, second, third, fourth, fifth, and sixth mounting surface and a first and second electrical circuit, the spring assembly further includes a third, fourth, fifth, and sixth electrical circuit. The first electrical circuit is affixed to the first mounting surface. The first electrical circuit includes the first inductive coil. The second electrical circuit is affixed to the second mounting surface. The second electrical circuit includes a second inductive coil. The third electrical circuit is affixed to the third mounting surface. The third electrical circuit includes a third inductive coil. The fourth electrical circuit is affixed to the fourth mounting surface. The fourth electrical circuit includes a fourth inductive coil. The fifth electrical circuit is affixed to the fifth mounting surface. The fifth electrical circuit includes a fifth inductive coil. The sixth electrical circuit is affixed to the sixth mounting surface. The sixth electrical circuit includes a sixth inductive coil.

In some embodiments including the first, second, third, fourth, fifth, and sixth electrical circuits, the spring assembly can further include a first, second, third, and fourth electrical circuit segment, each extending over an outer surface of the tubular body. The first electrical circuit segment joins the first electrical circuit to the third electrical circuit. The second electrical circuit segment joins the third electrical circuit to the fifth electrical circuit. The third electrical circuit segment joins the second electrical circuit to the fourth electrical circuit. The fourth electrical circuit segment joins the fourth electrical circuit to the sixth electrical circuit.

There is further provided, in accordance with some embodiments of the present disclosure, a force probe including a tubular segment, a first mounting surface in the tubular segment, a second mounting surface in the tubular segment, a compressible framework extending between the first and second mounting surfaces, a catheter, and an atraumatic probe tip. The tubular segment extends along a longitudinal axis. The tubular segment is sized to traverse vasculature. The first mounting surface is configured to engage a substantially planar electrical circuit. The first mounting surface positioned in a sidewall of the tubular segment, perpendicular to the longitudinal axis, and facing a first direction parallel to the longitudinal axis. The second mounting surface is configured to engage a substantially planar electrical circuit. The second mounting surface positioned in a sidewall of the tubular segment, perpendicular to the longitudinal axis, and facing toward the first mounting surface in a second direction opposite the first direction. The catheter is affixed to a first end of the tubular segment. The atraumatic probe tip is affixed to the second end of the tubular segment.

There is further provided, in accordance with some embodiments of the present disclosure an intravascular force probe including a proximal tube, an atraumatic distal end, a first inductive coil, a second inductive coil, and a compressible framework. The proximal portion includes an elongated body sized to traverse vasculature. The proximal tube and the atraumatic distal end define a longitudinal axis along which the force probe extends. The first inductive coil and the second inductive coil are each affixed between the proximal tube and the atraumatic distal end. The first inductive coil is confined in a first plane perpendicular to the longitudinal axis. The second inductive coil is confined in a second plane perpendicular to the longitudinal axis. The compressible framework is compressible parallel to the longitudinal axis to move the first inductive coil and the second inductive coil toward each other.

In some embodiments, the intravascular force probe further includes a catheter coupler affixed to the proximal tube and the atraumatic distal end. The catheter coupler includes the compressible framework. The catheter coupler structurally supports the first inductive coil and the second inductive coil.

In some embodiments, the intravascular force probe further includes a first connecting conductor electrically connecting the first inductive coil. The first connecting conductor extends circumferentially about the longitudinal axis within the first plane and is positioned outside an outer surface of the catheter coupler.

In some embodiments, the intravascular force probe further includes a third, fourth, fifth, and sixth inductive coil. The third and fifth inductive coils are confined in the first plane. The fourth and sixth inductive coils are confined in the second plane.

In some embodiments, the compressible framework is bendable to define a bend in the longitudinal axis, thereby causing the first plane and the second plane to be non-parallel.

In some embodiments, the intravascular force probe further includes a generator and an electrical measurement tool. The generator is electrically connected to the first inductive coil. The electrical measurement tool is electrically connected to the second inductive coil.

In some embodiments, the intravascular force probe further includes an electrical diagnostic system configured to receive a first electrical signal corresponding to a first distance between the first inductive coil and the second inductive coil, receive a second electrical signal corresponding to a second distance between the third inductive coil and the fourth inductive coil, receive a third electrical signal corresponding to a third distance between the fifth inductive coil and the sixth inductive coil, and determine a three dimensional force vector representing a force applied to the atraumatic distal end, the force vector determined based at least in part on the first electrical signal, the second electrical signal, and the third electrical signal.

There is further provided, in accordance with some embodiments of the present disclosure a catheter including a proximal tube, an atraumatic distal end, a first inductive coil, a second inductive coil, a compressible framework, a catheter coupler, and an elongated catheter tube.

The proximal tube and atraumatic distal end define a longitudinal axis.

The first inductive coil is affixed between the proximal tube and the atraumatic distal end. The first inductive coil is confined in a first plane perpendicular to the longitudinal axis.

The second inductive coil is affixed between the proximal tube and the atraumatic distal end and confined in a second plane perpendicular to the longitudinal axis.

The compressible framework is compressible parallel to the longitudinal axis to move the first inductive coil and the second inductive coil toward each other.

The catheter coupler is affixed to the proximal tube and the atraumatic distal end. The catheter coupler includes the compressible framework and structurally supports the first inductive coil and the second inductive coil.

The elongated catheter tube is affixed to the proximal tube, surrounds the first inductive coil, surrounds the second inductive coil, surrounds the compressible framework, surrounds the catheter coupler, and extends to a proximal end of the catheter.

The present disclosure will be more fully understood from the following detailed description of embodiments thereof, taken together with the drawings.

DETAILED DESCRIPTION

Figure 1:
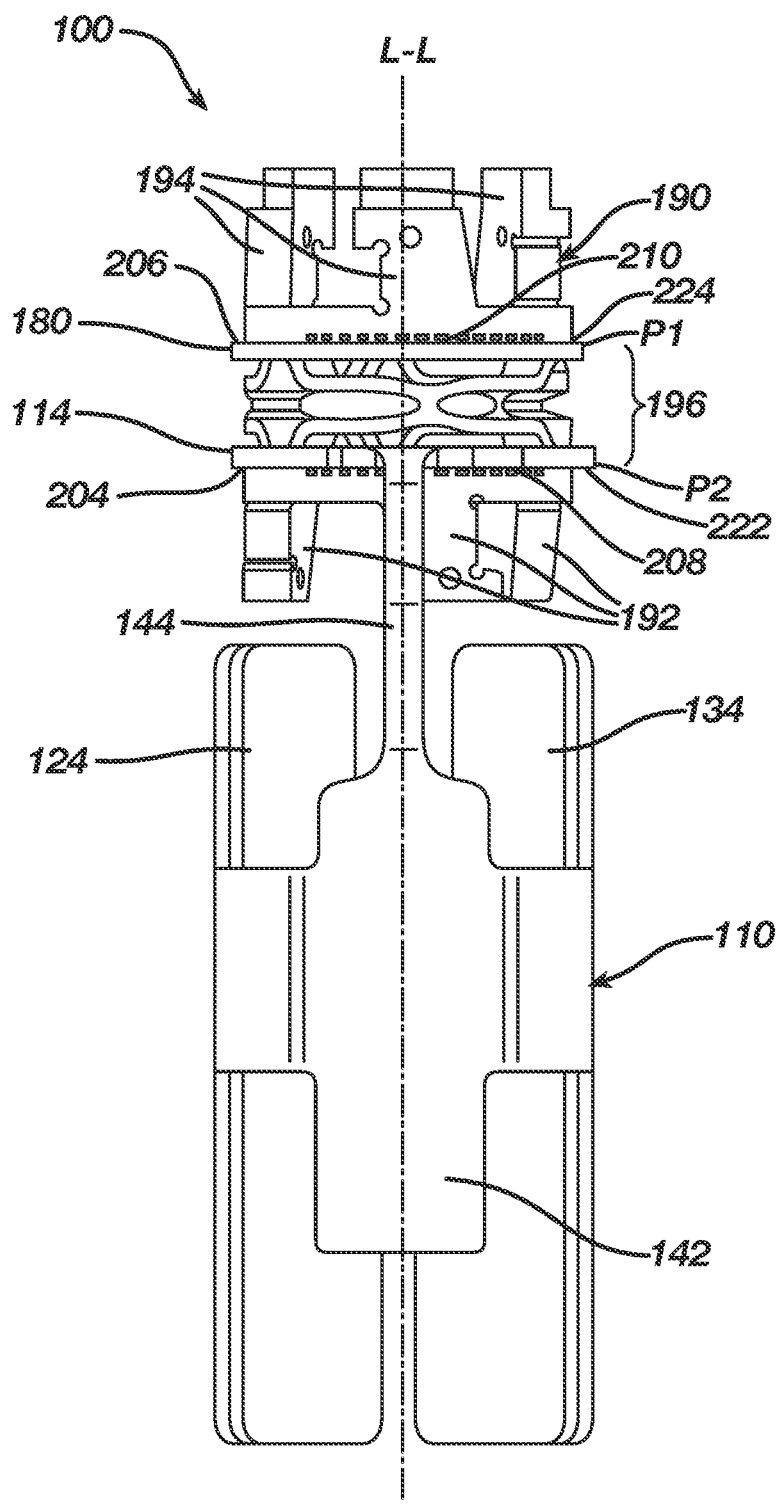
FIG. 1 is an illustration of a spring assembly in accordance with some embodiments of the present disclosure.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

As used herein, the term "computing system" is intended to include stand-alone machines or devices and/or a combination of machines, components, modules, systems, servers, processors, memory, detectors, user interfaces, computing device interfaces, network interfaces, hardware elements, software elements, firmware elements, and other computer-related units. By way of example, but not limitation, a computing system can include one or more of a general-purpose computer, a special-purpose computer, a processor, a portable electronic device, a portable electronic medical instrument, a stationary or semi-stationary electronic medical instrument, or other electronic data processing apparatus.

As used herein, the terms "component," "module," "system," "server," "processor," "memory," and the like are intended to include one or more computer-related units, such as but not limited to hardware, firmware, a combination of hardware and software, software, or software in execution. For example, a component may be, but is not limited to being, a process running on a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal. Computer readable medium can be non-transitory. Non-transitory computer-readable media include, but are not limited to, random access memory (RAM), read-only memory (ROM), electronically erasable programmable ROM (EEPROM), flash memory or other memory technology, compact disc ROM (CD-ROM), digital versatile disks (DVD) or other optical storage, magnetic cassettes, magnetic tape, magnetic disk storage or other magnetic storage devices, or any other tangible, physical medium which can be used to store computer readable instructions and/or data.

As used herein, the term "trace" includes a conductive path in an electrical circuit such as a path integral to a printed circuit, an individual wire, a conductor within a ribbon cable, or other such structure as appreciated and understood by a person of ordinary skill in the art according to the teachings of the present disclosure.

As used herein, the terms "tubular" and "tube" are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered outer surface, a curved outer surface, and/or a partially flat outer surface without departing from the scope of the present disclosure.

FIG. 1 illustrates a spring assembly 100 including a catheter coupler 190, a distal circuit 180 and a proximal circuit 110. The spring assembly 100 is sized to traverse vasculature; accordingly, all components and subcomponents thereof are sized to traverse vasculature. The catheter coupler 190 is compressible to cause the distal circuit 180 and an opposite portion 114 of the proximal circuit 110 to move in relation to each other. The distal circuit 180 and proximal circuit 110 are configured to provide an electrical signal indicative of one or more distances (or change in distance) at one more or locations between the distal circuit 180 and the opposite portion 114 of the proximal circuit 110.

The catheter coupler 190 has a tubular body defining a longitudinal axis L-L extending therethrough. The catheter coupler 190 is sized to traverse vasculature. The catheter coupler 190 includes a compressible framework 196 that can be compressed when force is applied to the spring assembly 100 along a longitudinal axis L-L. The compressible framework 196 can also be deflected by a force non-parallel to the longitudinal axis, causing the coupler 190 to bend. Because the longitudinal axis L-L is defined by the tubular body of the coupler 190, a bend in the coupler 190 thereby creates a bend in the longitudinal axis L-L.

The coupler 190 includes distal mounting surfaces 206, 210, 224 to which the distal circuit 180 is affixed and proximal mounting surfaces 204, 208, 222 to which a portion 114 of the proximal circuit 110 is affixed. The mounting surfaces 204, 206, 208, 210, 222, 224 are each configured to engage a substantially planar electrical circuit such as the distal circuit 180 and the opposite portion 114 of the proximal circuit 110. Each mounting surface 204, 206, 208, 210, 222, 224 is substantially perpendicular to the longitudinal axis L-L. Each of the proximal mounting surfaces 204, 208, 222 faces toward a respective mounting surface of the distal mounting surfaces 206, 210, 224 such that each of the proximal mounting surfaces 204, 208, 222 face a first direction parallel to the longitudinal axis and each of the distal mounting surfaces faces toward a respective proximal mounting surface 204, 208, 222 in a second direction opposite the first direction and parallel to the longitudinal axis. Each of the proximal mounting surfaces 204, 208, 222 can be sized and shaped as a mirror image of the facing distal mounting surface 206, 210, 224.

The coupler 190 can include three distal mounting surfaces 206, 210, 224 that are coplanar in a first plane P1 and three proximal mounting surfaces 204, 208, 222 that are coplanar in a second plane P2. The first and second planes P1, P2 are each perpendicular to the longitudinal axis L-L. A first distal surface 206 is positioned opposite a second proximal surface 204; a third distal surface 210 is positioned opposite a fourth proximal surface 208; and a fifth distal surface 224 is positioned opposite a sixth proximal surface 222. The first, third, and fifth surfaces 206, 210, 224 are coplanar in the first plane P1. The second, fourth, and sixth surfaces 204, 208, 222 are coplanar in the second plane P2. The first, second, third, fourth, fifth, and sixth mounting surfaces 204, 206, 208, 210, 222, 224 have substantially similar dimensions to each other. The first, third, and fifth mounting surfaces 206, 210, 224 are spaced 120° from each other as measured rotationally about the longitudinal axis. The second, fourth, and sixth mounting surfaces 204, 208, 222 are spaced 120° from each other as measured rotationally about the longitudinal axis.

Each mounting surface 204, 206, 208, 210, 222, 224 is positioned in a sidewall of the tubular body of the coupler 190.

The compressible framework 196 extends from the proximal mounting surfaces 204, 208, 222 to the distal mounting surfaces 206, 210, 224.

Figure 11:
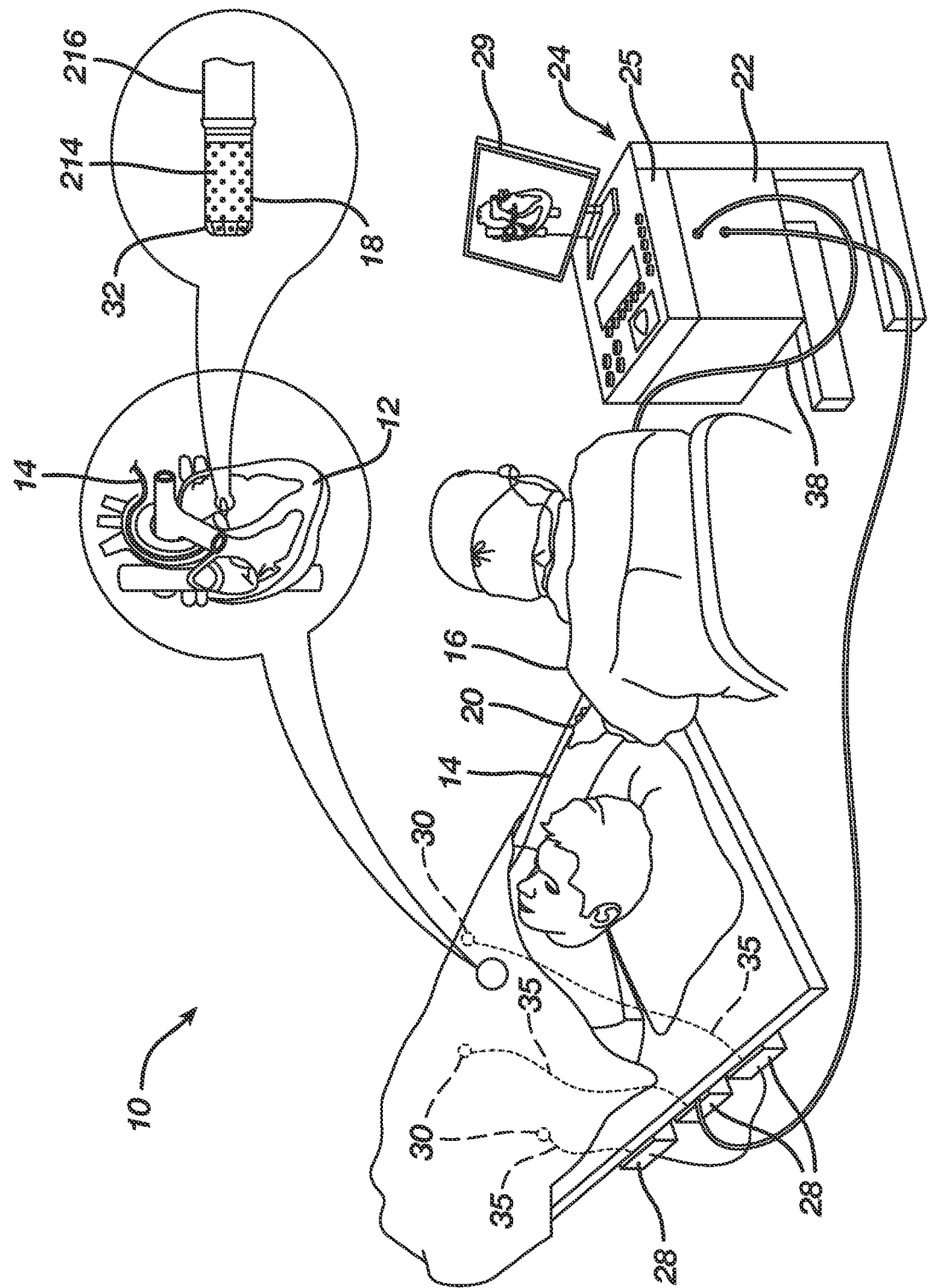
FIG. 11 is an illustration of a medical treatment utilizing the catheter and force probe in accordance with some embodiments of the present disclosure.

The catheter coupler 190 is further configured to join two portions of a catheter 14 (see FIG. 11). The catheter coupler 190 has distal engagement extensions 194 extending to a distal end of the tubular body and proximal engagement extensions 192 extending to a proximal end of the tubular body.

The distal circuit 180 and the opposite portion 114 of the proximal circuit 110 can include inductive coils positioned opposite each other. Each inductive coil can be positioned opposite another inductive coil with the compressible framework 196 therebetween. Opposite coils can be configured to act as an inductive distance sensor with one or more coils (preferably on the portion 114 of the proximal circuit 110) acting as a transmitter and one or more opposite coils (preferably on the distal circuit 180) acting as a receiver. A force probe including the spring assembly 100 can include a generator electrically connected to coil(s) acting as a transmitter and an electrical measurement tool electrically connected to coil(s) acting as a receiver.

Figure 5:
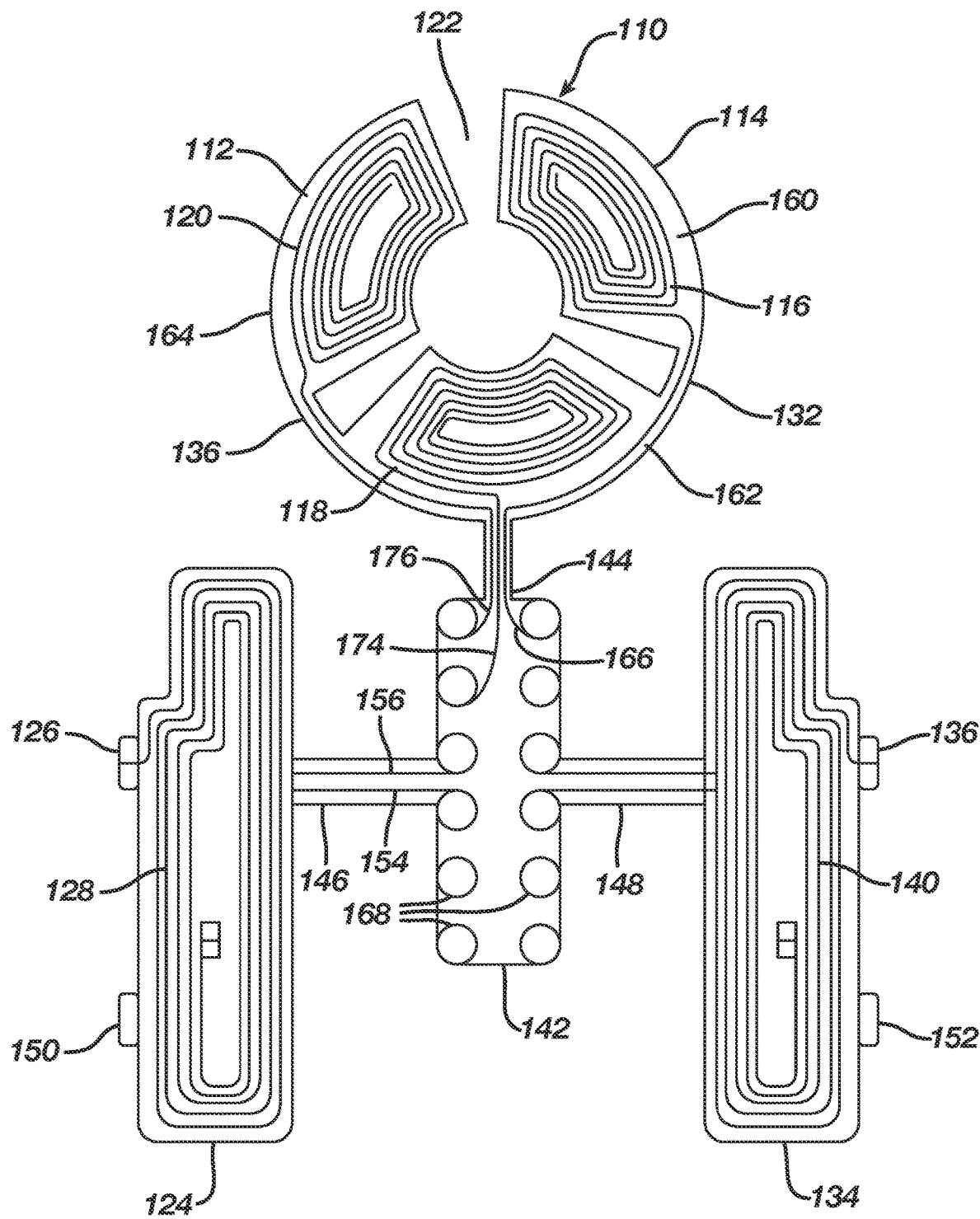
FIG. 5 is an illustration of an electrical circuit of the spring assembly in accordance with some embodiments of the present disclosure.

The distal circuit 180 can include three inductive coils 184 (see FIG. 8) and the opposite portion 114 of the proximal circuit 110 can include three inductive coils 116, 118, 120 (see FIG. 5). Each of the inductive coils 184 on the distal circuit 180 can be positioned opposite a respective inductive coil 116, 118, 120 on the proximal circuit 110. Inductive coils 184 on the distal circuit 180 can be confined to a plane perpendicular to the longitudinal axis L-L by virtue of being affixed to the distal mounting surfaces 206, 210, 224 of the coupler 190 (the distal mounting surfaces being coplanar in the first plane P1). Inductive coils 116, 118, 120 on the opposite portion 114 of the proximal circuit 110 can be confined to a plane perpendicular to the longitudinal axis L-L by virtue of being affixed to the proximal mounting surface 204, 208, 222 of the coupler 190 (the proximal mounting surfaces being coplanar in the second plane).

An intravascular force probe can include six inductive coils 184, 116, 118, 120 paired to form three inductive distance sensors. The force probe can further include an electrical diagnostic system configured to receive first, second, and third electrical signals corresponding to first, second, and third distances between first, second, and third coil pairs respectively. The electrical diagnostic system can further be configured to determine a three-dimensional force vector representing a force applied to a tip of the force probe based at least in part on the first, second, and third electrical signals.

The coupler 190 can structurally support the inductive coils 184, 116, 118, 120.

The proximal circuit 110 can further include additional circuit sections 124, 134, 142 for additional sensors and/or connections to an energy source. (See FIG. 5.)

Figure 2:
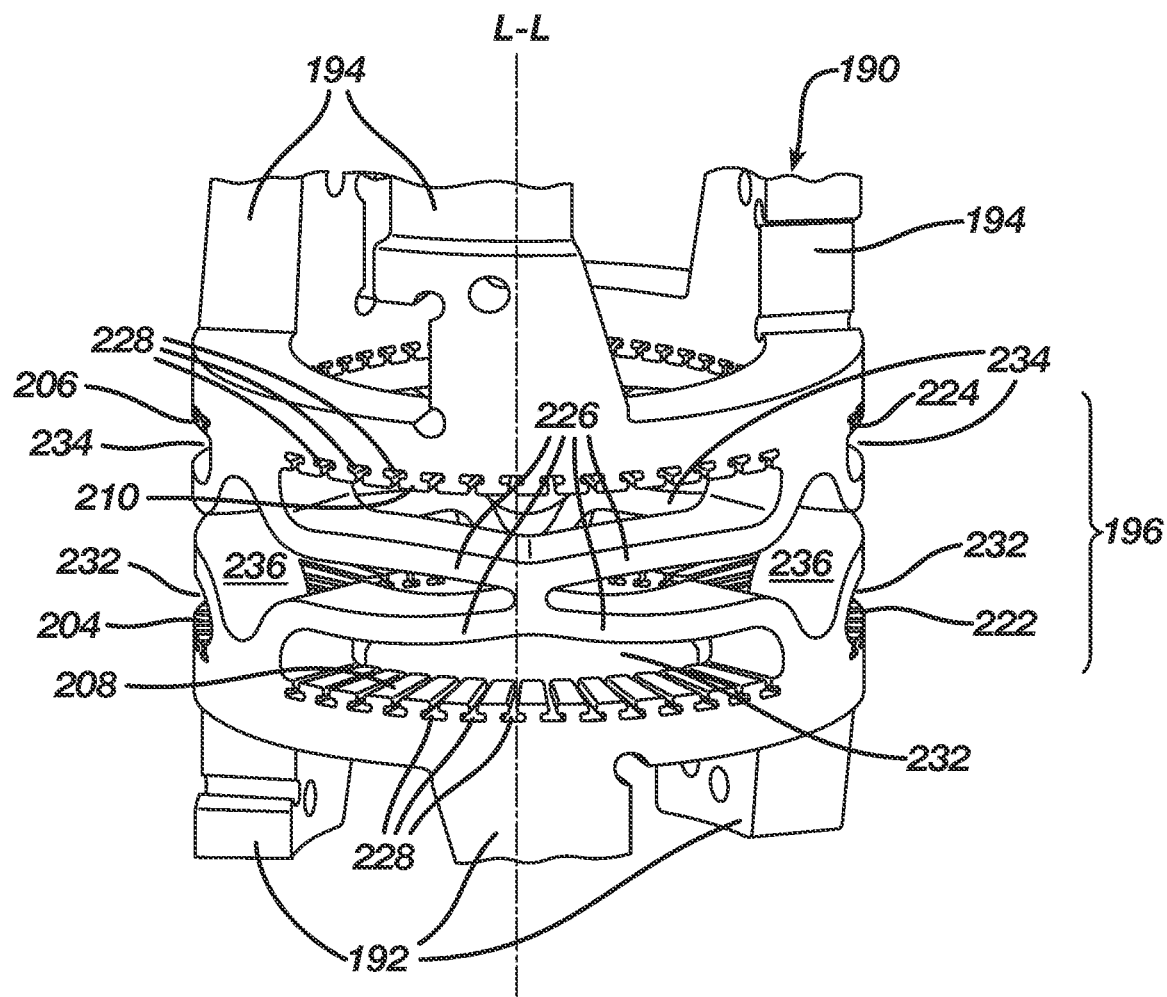
FIG. 2 is an illustration in an elevated profile view of a catheter coupler of the spring assembly in accordance with some embodiments of the present disclosure.
Figure 3:
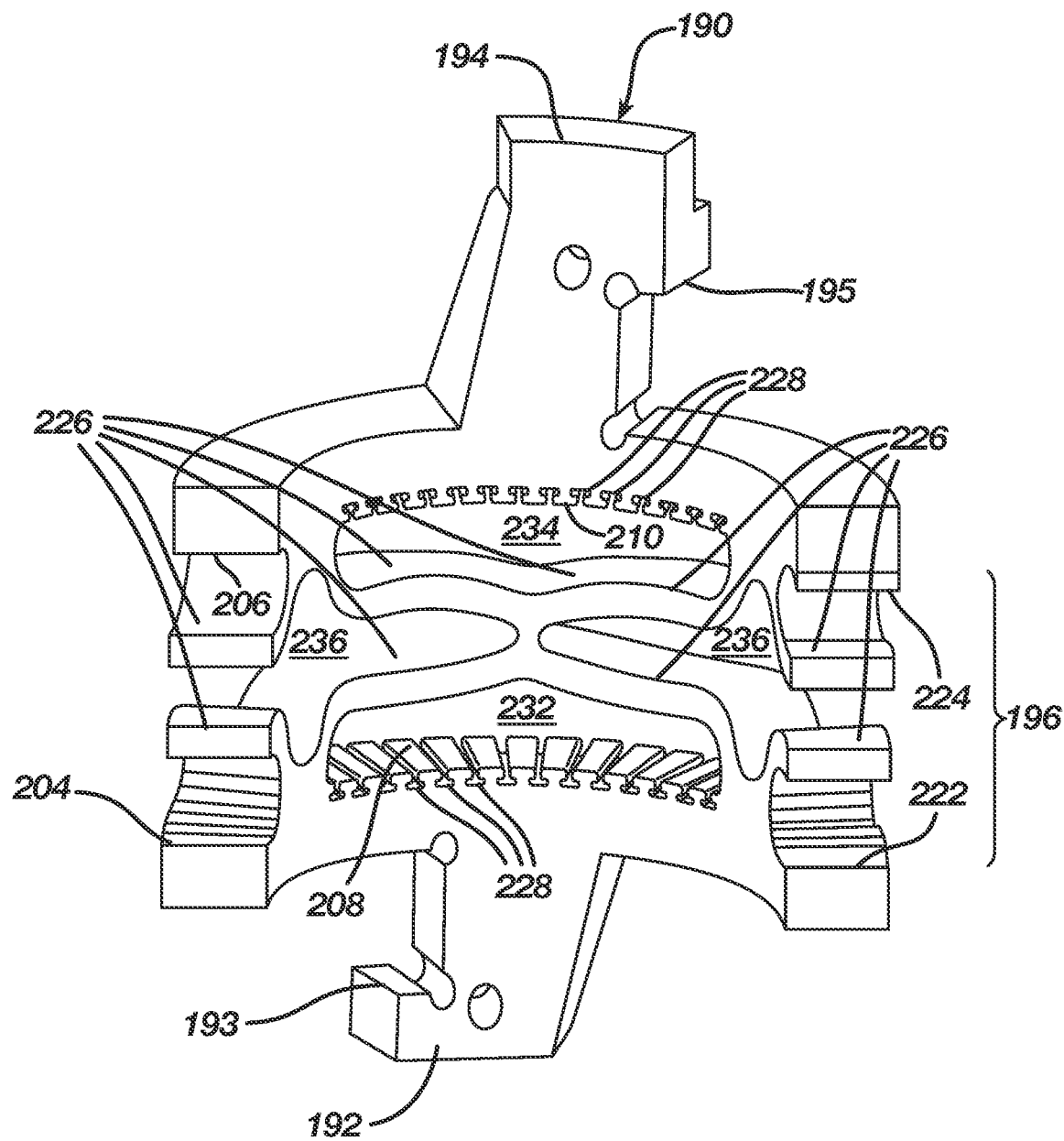
FIG. 3 is an illustration in a cross-sectional view of the catheter coupler in accordance with some embodiments of the present disclosure.

FIG. 2 is an illustration of the catheter coupler 190 in an elevated profile view. FIG. 3 is an illustration of a cross section of the catheter coupler 190 of FIG. 2. Referring collectively to FIGS. 2 and 3, the tubular body of the coupler 190 includes openings 232, 234, 236 in the area of the compressible framework 196. As illustrated, the tubular body includes three proximal openings 232 each circumscribed by one of the proximal mounting surfaces 204, 208, 222 and struts 226 of the compressible framework 196. As illustrated, the tubular body includes three distal openings 234 each circumscribed by one of the distal mounting surfaces 206, 210, 224 and struts 226 of the compressible framework. As illustrated, the tubular body includes three central openings 236 each circumscribed by struts 226 of the compressible framework 196.

Struts 226 and openings 232, 234, 236 in the compressible framework can be alternatively configured to allow compression and/or bending of the compressible framework 196 when the spring assembly 100 is manipulated as part of a catheter force probe. The struts 236 can be, sized, shaped, positioned, and otherwise configured to provide a predetermined travel length (in the direction of the longitudinal axis L-L and/or off-axis) and/or a predetermined spring constant. The spring constant and/or travel length can be determined based on clinical working range required for a specific application or range of applications. The struts 236 can be designed to result in a specific travel length and spring constant based on the clinical working range of contact force (e.g., 500g or less) required in specific applications.

Some or all of the openings 232, 234, 236 in the tubular body can collapse when the compressible framework 196 is compressed. Openings 232, 234 circumscribed in part by one of the mounting surfaces 204, 206, 208, 210, 222, 224 can collapse when the compressible framework 196 is compressed. Additionally, or alternatively, openings 236 circumscribed by struts 226 of the compressible framework 196 can collapse when the compressible framework 196 is compressed.

Each mounting surface 204, 206, 208, 210, 222, 224 can be configured to receive a liquid adhesive suitable for adhering the distal and proximal circuits 180, 110. Each mounting surface 204, 206, 208, 210, 222, 224 can include T-shaped indentations 228 into which adhesive can flow. The T-shaped indentations 228 can provide improved securement of adhesion to the mounting surfaces 204, 206, 208, 210, 222, 224 compared to smooth planar mounting surfaces. Each mounting surface 204, 206, 208, 210, 222, 224 can otherwise be treated to improve adhesion as appreciated and understood by a person of ordinary skill in the art according to the teachings of the present disclosure.

The coupler 190 can further include multiple engagement extensions 194 extending from a first end of the tubular body, parallel to the longitudinal axis L-L and multiple engagement extensions 192 extending from a second end of the tubular body, parallel to the longitudinal axis L-L. Each engagement extension 192, 194 on either side of the tubular body can include a protrusion 192, 195 extending therefrom in a circumferential direction about the longitudinal axis. The spring assembly can include exactly three engagement extensions 192 extending from the first end of the tubular body and exactly three engagement extensions 194 extending from the second end of the tubular body.

Figure 4:
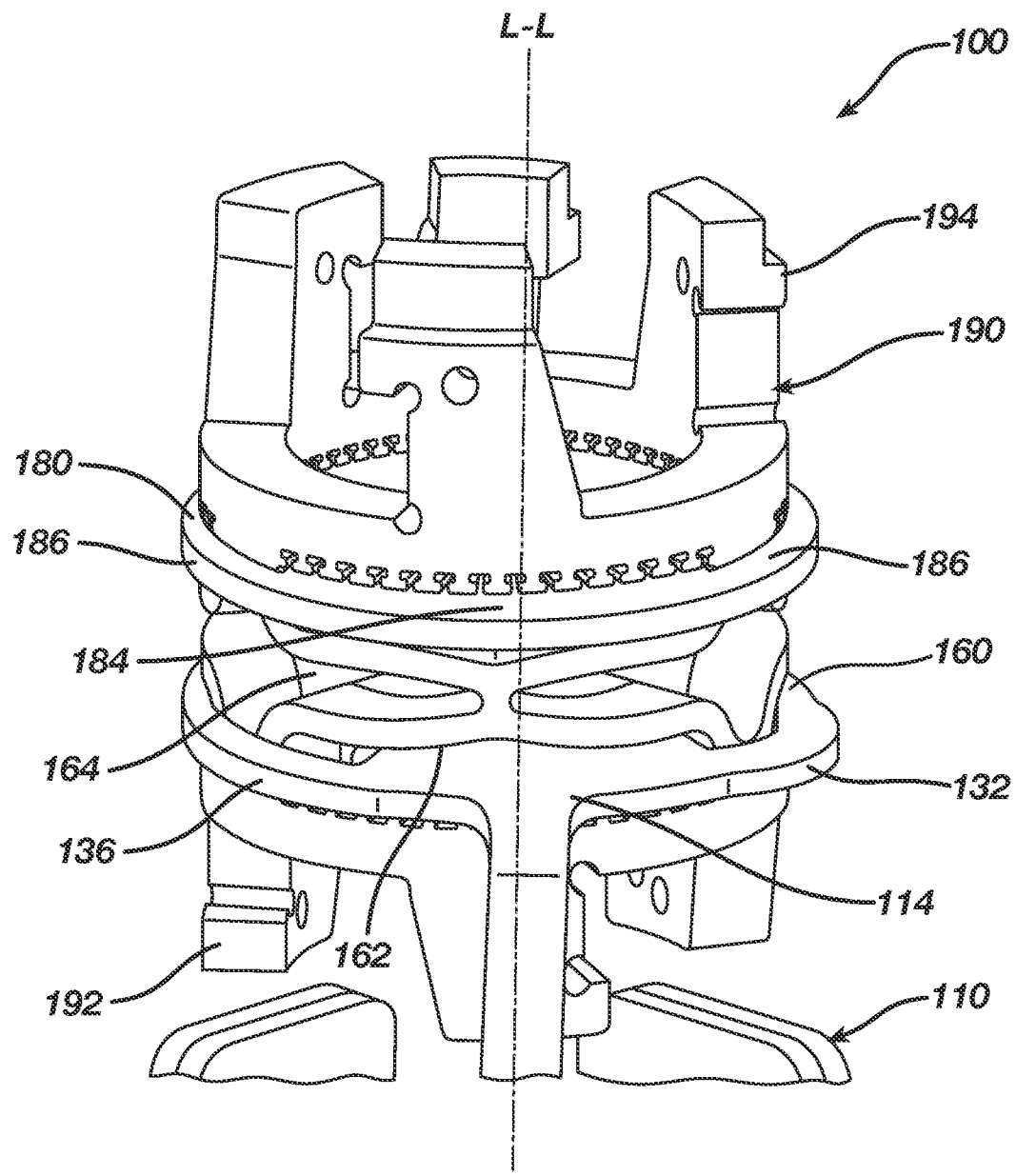
FIG. 4 is an illustration of the spring assembly in an elevated profile view in accordance with some embodiments of the present disclosure.

FIG. 4 is an elevated profile view of a distal portion of the spring assembly 100 to provide a view of the position of the distal circuit 180 and opposite portion 114 of the proximal circuit 110 within the spring assembly 100. In this view, four electrical circuit segments 132, 136, 186 can be seen extending outside an outer surface of the tubular body of the coupler 190.

Figure 8:
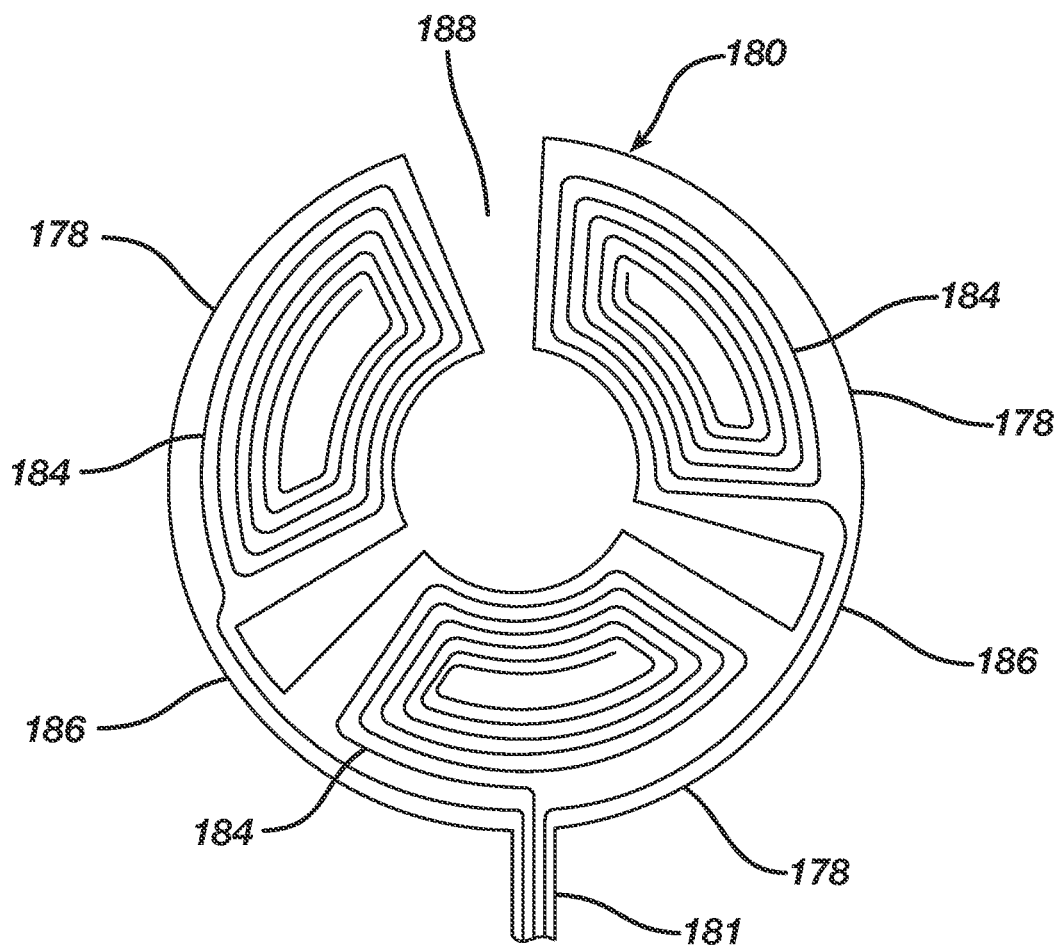
FIG. 8 is an illustration of another electrical circuit of the spring assembly in accordance with some embodiments of the present disclosure.

The distal electrical circuit 180 is illustrated in greater detail in FIG. 8. Referring collectively to FIGS. 4 and 8, the distal electrical circuit 180 includes two segments 186 each extending over an outer surface of the tubular body of the coupler 190. The two segments 186 each connect two larger portions 178 of the distal electrical circuit 180 such that three larger portions 178 of the distal electrical circuit 180 are connected by the two segments 186. Inductive coils 184 of the distal circuit 180 are positioned in the larger portions 178 of the distal circuit 180.

The proximal circuit 110 is illustrated in greater detail in FIG. 5. Referring collectively to FIGS. 4 and 5, the portion 114 of the proximal circuit 110 positioned opposite the distal circuit 180 includes two connecting segments 132, 136. The first connecting segment 132 of the proximal circuit 110 joins a first larger portion 164 to a second larger portion 162. The second segment 136 of the proximal circuit 110 joins the second larger portion 162 to a third larger portion 160.

The larger portions 160, 162, 164, 178 can each be shaped to extend across each respective mounting surface 204, 206, 208, 210, 222, 224 into a lumen 212 defined by the inner surface of the coupler 190 when the respective circuits 180, 114 are mounted to the coupler 190. The connecting segments 132, 136, 186 are positioned to extend over an outer surface of the coupler 190. Each segment 132, 136, 186 and its pair of adjacent larger portions 160, 162, 164, 178 forms a notch into which portions of the strut framework 196 between mounting surfaces 204, 206, 208, 210, 222, 224 can be positioned. Configured as such, the circuits 180, 114 can be aligned parallel to each other in planes P1, P2 (FIG. 1) perpendicular to the longitudinal axis L-L. Circuits 114, 180 can be positioned closer to each other compared to some other known force sensor designs.

FIG. 5 is an illustration of a flexible circuit 110 that can be used as the proximal circuit 110 in the spring assembly 100. The flexible circuit 110 can be employed within a catheter to provide signals concerning force to a processor at a physician console. The flexible circuit 110 can also include circuitry to provide signals concerning location. The flexible circuit 110 includes a substantially planar substrate 112 including a substantially circular portion 114. The circular portion 114 is shaped to be mounted in the catheter coupler 190 opposite the distal circuit 180 as illustrated in FIGS. 1 and 4. The substrate 112 includes additional portions 124, 134, 142 shaped to wrap around the longitudinal axis L-L. The additional portions 124, 134, 142 can have a substantially rectangular shape as illustrated or other shape. Portions 114, 124, 134, 142 can be joined by connector segments 144, 146, 148. The width of the rectangular portions 124, 134, 142 and associated connector segments 146, 148 can be sized such that when wrapped within or around a catheter, sleeve, sheath, or other such tubular structure, the additional portions 124, 134, 142 almost completely circumscribe the longitudinal axis L-L. The substrate 112 can be formed of a suitable material that is non-conductive and is capable of resisting high temperatures, e.g. polyimide, polyamide, or liquid crystal polymer (LCP). Alternatively, some or all of the portions 114, 124, 134, 142 and segments 144, 146, 148 can be constructed on a substrate separate from substrate 112 and joined to form circuit 110 by processes known to a person of ordinary skill in the art.

The circular portion 114 of the circuit 110 includes the three larger portions 160, 162, 164 and two connecting segments 132, 136 as illustrated and described in relation to FIG. 4. Each of the three larger portions 160, 162, 164 is an annular sector of the circular portion 114. The annular sectors 160, 162, 164 can have a substantially identical shape to each other. The first annular sector 164 is separated from the third annular sector 160 by an opening 122 in the circular portion 114. The segments 132, 136 can be flexible so that the circular portion 114 can be opened for insertion into the coupler 190 and positioned to a final position as illustrated in FIG. 4.

Figure 6A:
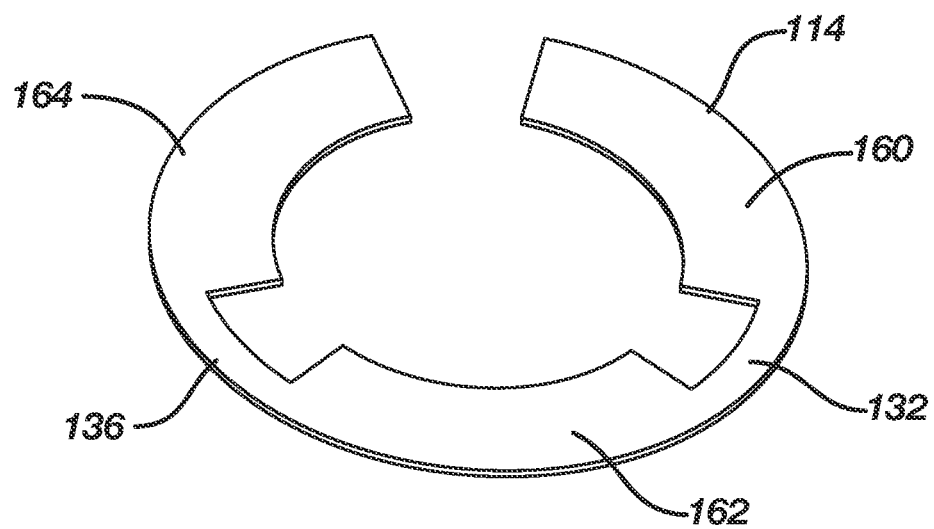
FIGS. 6A and 6B are illustration of a sequence for opening an electrical circuit for insertion into the spring assembly in accordance with some embodiments of the present disclosure.
Figure 6B:
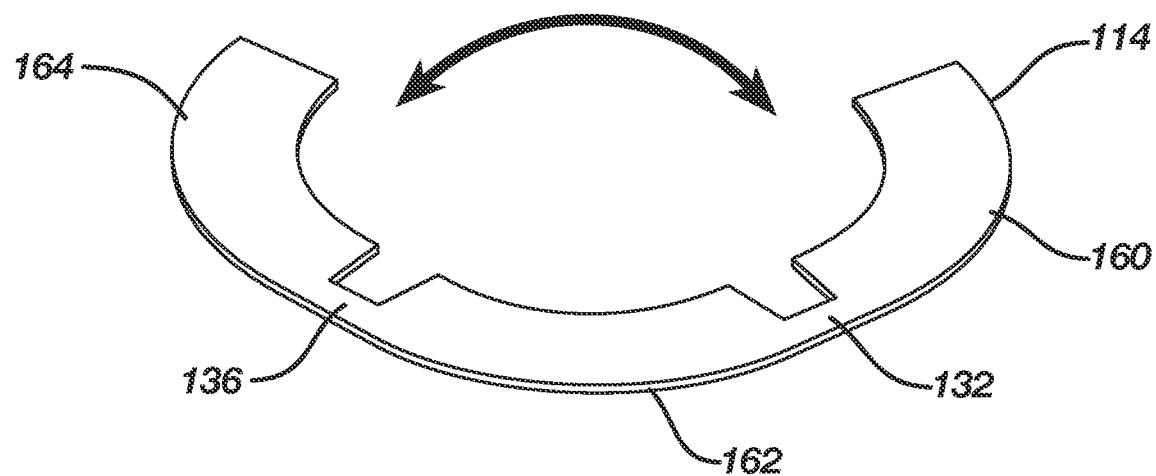

FIG. 6A is an illustration of the circular portion 114 in an elevated view in a relaxed shape as illustrated in FIG. 5. FIG. 6B is an illustration in an elevated view of the circular portion 114 opened for insertion into the coupler 190.

The entire circular portion 114 can be flexible. Alternatively, the annular sectors 160, 162, 164 can be rigid, not substantially elastically deformable. Regardless as to whether annular sectors 160, 162, 164 are rigid or flexible when manufactured, when affixed to coupler 190, the annular sectors 160, 162, 164 can be sufficiently rigid to maintain position of the inductive coils in the second plane P2 (see FIG. 1) during shipping, handling pre-treatment, and manipulation during treatment. Segments 132, 136 can be sufficiently flexible to allow the circular portion 114 to be installed into the coupler 190.

Segments 132, 136 can be rigidly affixed to coupler 190. Alternatively, segments 132, 136 can be flexible, providing strain relief between the annular sectors 178 when the annular sectors 178 are affixed to the coupler. For instance, segments 132, 136 can include an S configuration that can be positioned flat against the outer diameter of the coupler 190.

Figure 7:
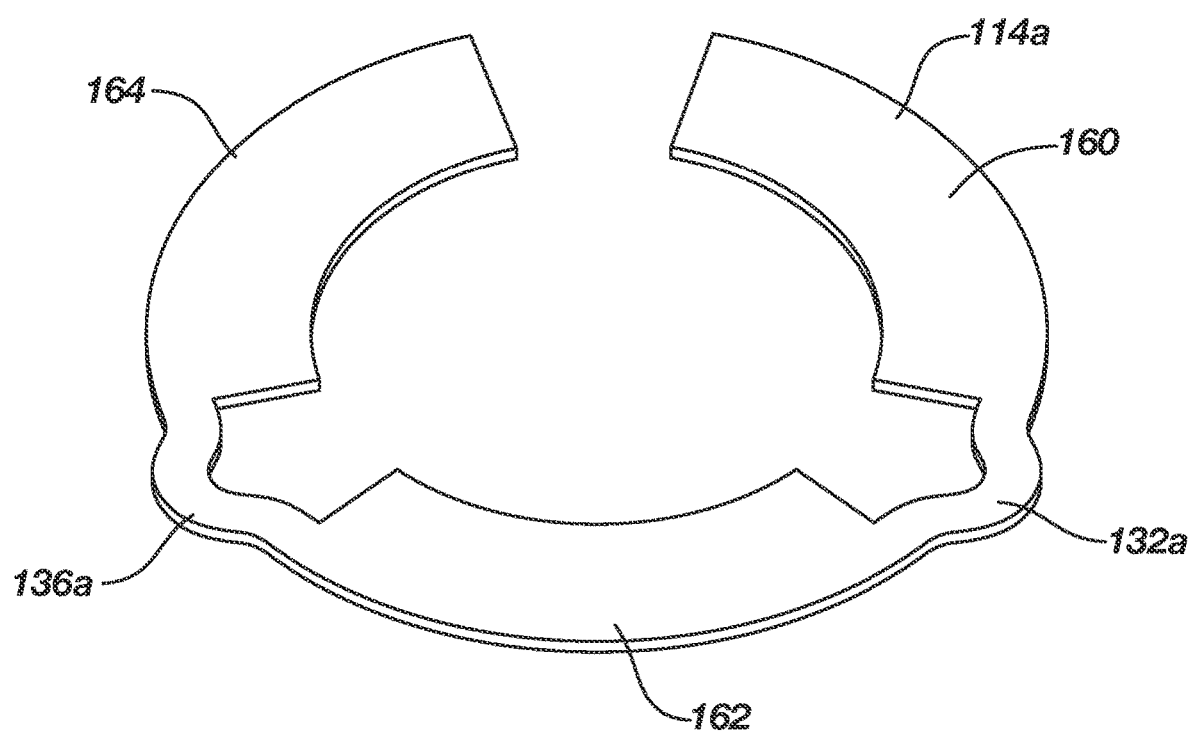
FIG. 7 is an illustration of an electrical circuit having connecting segments shaped for strain relief in accordance with some embodiments of the present disclosure.

FIG. 7 illustrates is an illustration of a circular circuit 114a in an elevated view having segments 132a, 136a that extend radially outwardly. The segments 132a, 136a are shaped to provide strain relief. When the circular circuit 114a is affixed to the coupler 190, the segments 132a, 136a are separated from the outer surface of the coupler 190 over at least a portion of the length of each respective segment 132a, 136a. The segments 132, 136 can be alternatively shaped such that the segments are able to lengthen as the coupler 190 bends.

Each annular sector 160, 162, 164 includes an inductive coil 116, 118, 120. The coils 116, 118, 120 can be discrete from each other, as shown, or they can each be connected to one or both of the others. As shown, each coil 116, 118, 120 on circular portion 114 includes approximately five turns. However, because signal strength is a function of the number of turns, the number of turns can be maximized based on the size of each segment and the pitch that the lithographic process can accomplish.

Each segment 132, 136 can include a connecting trace 166, 176 electrically connected to one or more of the inductive coils 116, 120. A trace 166, 176 in a connecting segment 132, 136 can extend circumferentially about the longitudinal axis at a position outside an outer surface of the catheter coupler. As illustrated in FIGS. 4 and 5, such a trace 166, 176 can be confined in a plane with the inductive coils 116, 118, 120 on the circular portion 114 of the proximal circuit 110 when the proximal circuit 114 is affixed to the coupler 190. Alternatively, if the connective segment 132, 136 in which the connecting trace 166, 176 is positioned is non-planar (e.g. is shaped for strain relief), the trace 166, 176 can have a non-planar shape, following the shape of the respective connecting segment 132, 136.

The circuit 110 includes a connector segment 144 joining the circular portion 114 to a rectangular portion 142 of the circuit. The connector segment 144 can be sufficiently flexible to bend from a planar shape to include a curve turning at about 90°. Alternatively, the circuit 110 can include a 90° curve in the segment 144 as fabricated. When each inductive coil 116, 118, 120 is discrete, the segment 144 can include three traces 166, 174, 176, each trace electrically connected to a respective inductive coil 116, 118, 120 in the circular portion 114 of the circuit 110. When two or more of the coils 116, 118, 120 are electrically connected, the segment 144 can include one or two traces.

The rectangular portion 142 connected directly to the circular portion 114 includes solder joints 168. Where the three coils are discrete from each other, each respective extension 166, 174, and 176 is joined to a separate solder joint 168. Alternatively, extensions 166, 174, 176 can join two or more coils 116, 118, 120, in which case, fewer solder joints 168 can be included in the rectangular portion 142. Where the coils 116, 118, 120 are discrete from each other, the signals generated in each of the coils may be used to provide additional details of force, such as an indication of an off-center force or an off-axis direction of the force.

The distal circuit 180, and the circular portion 114 of the proximal circuit 110 are sufficient to serve as distance measurement transducers that when assembled in the coupler 190 can provide electrical signals indicative of deflection of the coupler. Structural properties of the compressible framework 196 and geometry of the catheter force probe can be known such that a deflection and/or compression of the compressible framework 196 is associated with a force or force vector applied to the catheter force probe.

Planar coils or traces used to measure signals relating to location (i.e., location coils or traces) can be incorporated into additional rectangular portions 124, 134 of the circuit 110. Alternatively, the rectangular portions 124, 134 with coils can be omitted if only force sensing is desired.

A left rectangular coil 128 can be incorporated with a left portion 124 and a right coil 140 can be incorporated with a right portion 134 (where right and left are oriented in relation to the illustration in FIG. 5). The circuit 110 can include extensions 156, 154 positioned in a joining segment 146 joining the left portion 124 to the central rectangular portion 142. The extensions 156, 154 connect the left rectangular coil 128 to solder pads 168 in the central rectangular portion 142. Likewise, the circuit 110 can include extensions positioned in the opposite joining segment 148 and connecting the right rectangular coil 140 to the solder pads 168. As shown, each coil 128, 140 on the rectangular portions 124, 134 includes approximately five turns. However, because signal strength is a function of the number of turns, the number of turns may be maximized based on the size of the rectangular portions 124, 134, and the pitch that the lithographic process can accomplish.

The wind of coils 116, 118, 120, 128, 140 can be clockwise (i.e., have a clockwise orientation) or counterclockwise. The orientation of coils can be selected as appreciated and understood by a person of ordinary skill in the art to perform sensor functionality described herein.

Substrate 112 can be a single layer. Alternatively, the substrate 112 can include between two and ten layers, e.g., four layers. In this manner the coils can be thickened by adding layers. However, thickening by layers can result in increased non-linearity of signal yield. As another alternative, the circuit 110 can include additional portions (not illustrated) each including one or more inductive coils. The additional portions can each be connected respectively to an illustrated portion 114, 124, 134 and positioned underneath the respective illustrated portion. The circuit 110 can have sufficient flexibility at connection(s) between the additional portions and the illustrated portions to bend 360° for placement of the additional portions underneath the respective illustrated portion 114, 124, 134. For instance, tabs 126, 136, 150, 152 extending from the left and right rectangular portions 124, 134 can be folded segments joining to additional left and right rectangular portions each respectively positioned under the illustrated left and right rectangular portions 124, 134. Coils within overlapping portions can be aligned. By stacking substrates, panelization density due to increased area may increase, and the yield of the combined coil may not suffer from increased non-linearity as extensively compared to coils stacked within a substrate.

FIG. 8 is an illustration of a circular circuit 180 that can be used as the distal circuit 180 of the spring assembly 100. The circuit 180 includes the three larger portions 178 and two segments 186 as illustrated and described in relation to FIG. 4. Each of the three larger portions 178 is an annular sector of the circuit 180. Two of the annular sectors 178 are separated by an opening 188 in the circuit 180.

The segments 186 can be flexible so that the circuit 180 can be opened for insertion into the coupler 190 and positioned as illustrated in FIG. 4. The entire circuit 180 can be flexible. Alternatively, the annular sectors 178 can be rigid, not substantially elastically deformable. Regardless as to whether annular sectors 178 are rigid or flexible when manufactured, when affixed to coupler 190, the annular sectors 178 can be sufficiently rigid to maintain position of the inductive coils in the second plane P2 (see FIG. 1) during shipping, handling pre-treatment, and manipulation during treatment. Segments 186 can be sufficiently flexible to allow the circuit 180 to be installed into the coupler 190. Segments 186 can be rigidly affixed to coupler 190. Alternatively, segments 186 can be flexible, providing strain relief between the annular sectors 178.

The circuit 180 can be opened similar to the circular portion 114 illustrated in FIGS. 6A and 6B. The segments 186 can be shaped for strain relief similar to the connecting segments 132a, 136a illustrated in FIG. 7 and otherwise described in relation to the connecting segments 132, 136 of the circular portion 114, 114a.

Each annular sector 178 includes an inductive coil 184. The coils 184 can be discrete from each other, as shown, or they can each be connected to one or both of the others. As shown, each coil 184 includes approximately five turns. However, because signal strength is a function of the number of turns, the number of turns can be maximized based on the size of each segment and the pitch that the lithographic process can accomplish.

Each segment 186 can include a trace electrically connected to one or more of the inductive coils 116, 120.

The distal circuit 180 can further include an extension 181 through which traces to the coils 184 can be routed. The extension 181 can bend to extend longitudinally past the proximal end of the coupler 190 and ultimately to solder joints (not shown). The extension 181 can be adhered or otherwise joined to the proximal circuit 110 such that traces extending through the extension are connected to solder joints 168 on the proximal circuit 110. Alternatively, the distal circuit 180 can include a solder pad portion and/or additional inductive coil portions such as corresponding portions 142, 124, 134 of the proximal circuit 110. As another alternative, where location sensing is not incorporated with the spring assembly, both the proximal circuit 110 and the distal circuit 180 can be configured substantially similar to the example distal circuit 180 illustrated in FIG. 8 with solder joints connecting to traces in the extension 181.

Figure 9:
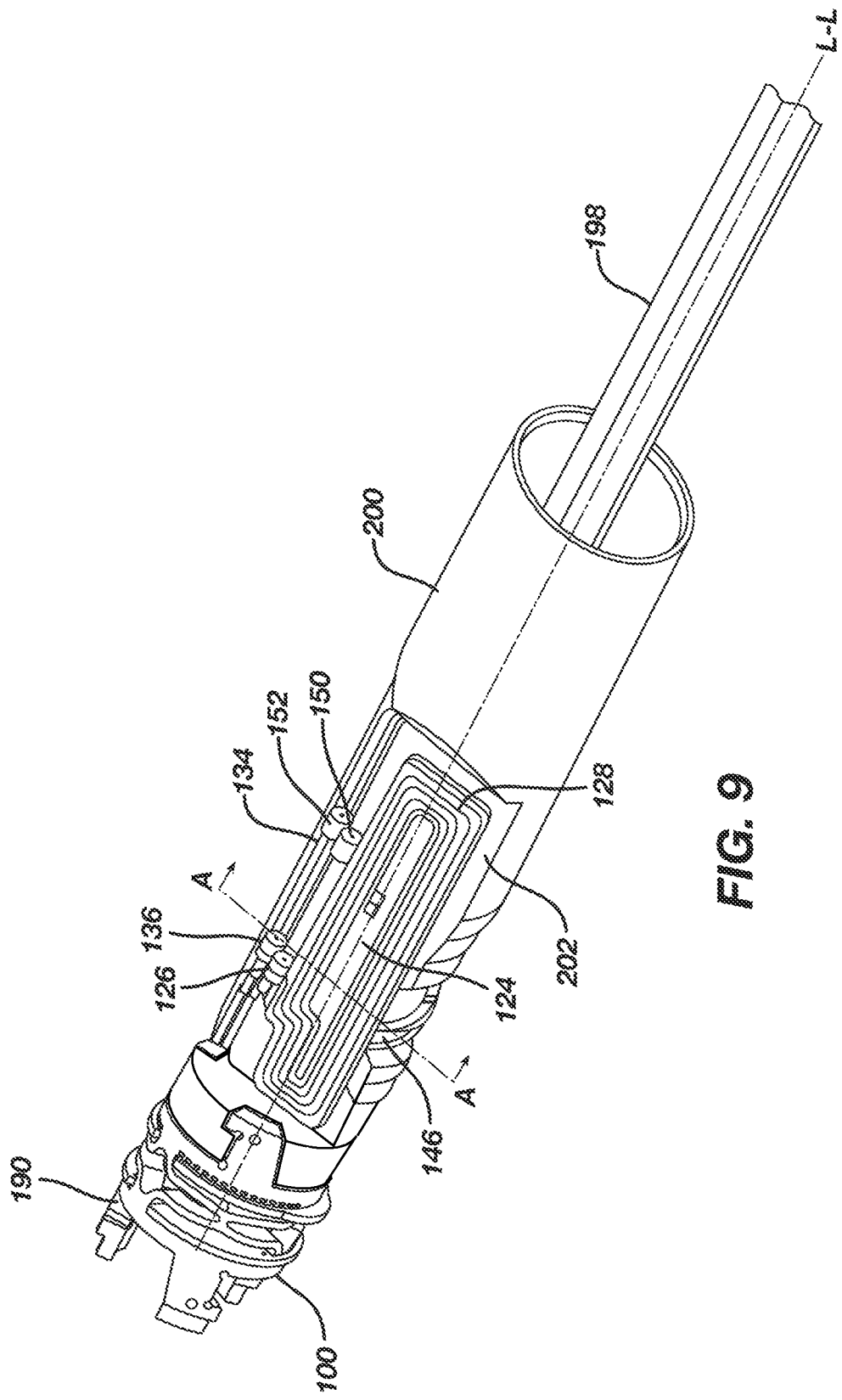
FIG. 9 is an illustration of components of a force probe of a partially assembled catheter including the spring assembly in accordance with some embodiments of the present disclosure.
Figure 10:
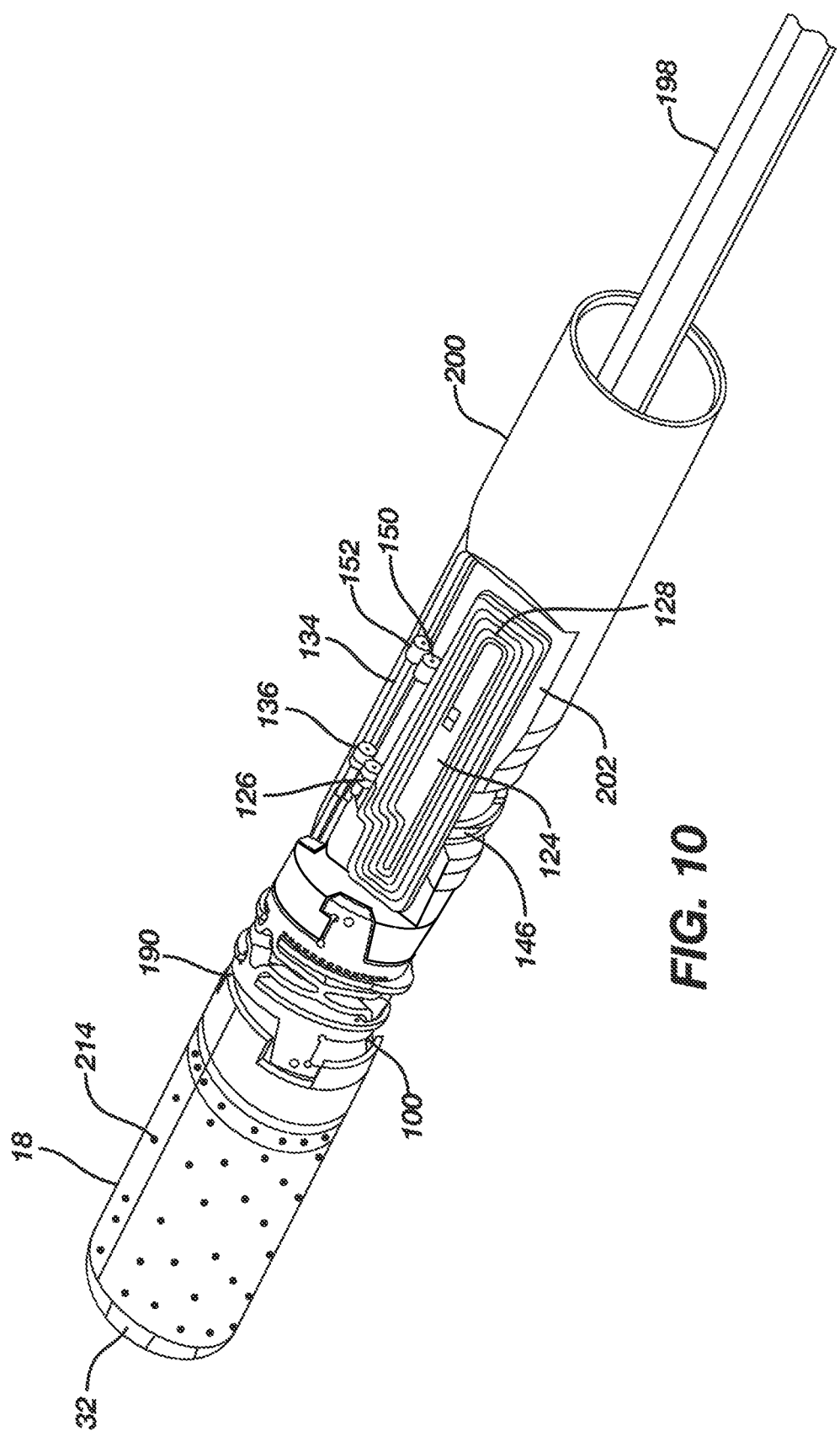
FIG. 10 is another illustration of components of the force probe of a partially assembled catheter including the spring assembly in accordance with some embodiments of the present disclosure.

FIGS. 9 and 10 show a catheter 14 (see FIG. 11) at two different steps of its assembly, illustrating components of a force probe including the spring assembly 100. FIG. 9 shows the proximal flexible circuit 110 as assembled to coupler 190 and a coupling sleeve 200. The circular portion 114 of the proximal circuit 110 and the distal circuit 180 are each adhered to the coupler 190 as illustrated in FIGS. 1 and 4.

As illustrated in FIG. 10, the force probe can include a distal portion 18, which can include ablation electrode(s) 32 and irrigation apertures 214. The distal end 32 of the distal portion can be atraumatic. The force probe can further include a tubular proximal portion, coupling sleeve 200 sized to be positioned within an elongated catheter body 216 and shaped such that rectangular portions 124, 134, 142 can be mounted thereon. The force probe can include a pair of planar inductive coils affixed between the proximal portion 200 and the atraumatic distal end 32 such that each coil in the pair is in a plane perpendicular to the longitudinal axis L-L. The force probe can include the compressible framework 196 which is compressible parallel to the longitudinal axis to move the inductive coils in the pair toward each other.

The force probe can further include catheter coupler 190. The coupler can be attached to the spring assembly 100 via the engagement extensions 194 extending from a distal end of the coupler 190. Protrusions 195 of the distal engagement extensions 194 each engage a complementary feature of the tip 18. The coupler 190 can be attached to the tubular proximal portion 200 via the engagement extensions 192 extending from a proximal end of the coupler 190. Protrusions 193 of the proximal engagement extensions 192 each engage a complementary feature of the tubular proximal portion 200.

The catheter 14 can include a cable bundle 198 including a set of cables connecting to the force probe, which, although not visible, are connected to solder joints 168 on the associated rectangular portion 142 of the proximal circuit 110 and thus to the various coils or traces on the proximal circuit 110. The cable bundle 198 also includes cables connected to traces to coils 184 of the distal circuit 180.

Rectangular portions 124, 134, 142 of the proximal circuit 110 are affixed to substantially planar surfaces 202 of the coupling sleeve 200 either direly adhered, or by virtue of attachment of an underlying layered substrate adhered to the surface 202. So assembled, these portions 124, 134, 142 of flexible circuit 110 may be viewed as having a triangular cross section as viewed in plane A-A. perpendicular to the longitudinal axis L-L. Connecting segments 146, 148 can be adhered to arcuate surfaces of sleeve 200 positioned at corners of the triangular cross section of the planar portions 124, 134, 142 as viewed in plane A-A indicated in FIG. 9.

Accordingly, as assembled, flexible circuit 110, may be readily inserted into an outer tube or sleeve 216 (FIG. 11) that provides an outer surface of catheter 14 and that defines the inner diameter within which componentry (e.g., flexible circuits 110, 180, coupler 190, sleeve 200) of catheter 14 resides. All of the components describe herein are disposed inside a sleeve 216 of approximately 15 French or smaller. To help prevent soft spots under sleeve 216 that result from gaps between the substantially planar outer surfaces of rectangular portions 124, 134, 142 of the proximal circuit 110 on the one hand, and the curvature of sleeve 216 on the other hand, these gaps may be filled by including additional material, e.g., adhesives and/or polyimide layers on the rectangular portions 124, 134, 142. The additional material may be fabricated separately from flexible circuit 110 and adhered thereto, or they may be an integral portion of flexible circuit 110, formed during the same lithographic process as the remainder of flexible circuit 110.

Flexible circuit 110 may be assembled into catheter 14 as follows. First, flexible circuit 110 may be provided. If portions of the circuit 110 are to be folded to form layered substrates, such portions can be folded accordingly. Adhesive can be applied to annular sectors 160, 162, 164 and/or proximal mounting surfaces 204, 208, 222 of the coupler 190. Annular sectors 160, 162, 164 can be spread apart by flexing the connecting segments 132, 136 to widen the opening 122 (FIGS. 6A and 6B). Each annular sector 160, 162, 164 can be respectively wedged into an opening 232 in the tubular body of the coupler 190 circumscribed by a proximal mounting surface 204, 208, 222 and struts 226 of the compressible framework 196. The connecting segments 132, 136 can be bent and/or twisted as the annular sectors 160, 162, 164 are moved into position. The connecting segments 132, 136 can relaxed to a non-stressed shape once the sectors 160, 162, 164 are in position. Adhesive can cure to join each annular sector 160, 162, 164 of the proximal circuit 110 to a respective mounting surface 222, 208, 204 of the coupler 190. Annular sectors 160, 162, 164 can be coplanar when adhered to the coupler 190. Adhesive can be applied to a backside of the rectangular portions 124, 142, 134 and/or the connecting segments 146, 148 therebetween. The segment 144 connecting the circular portion 114 of the proximal circuit 110 to the portion 142 having solder joints 168 thereon can be bent at about 90°. The rectangular segments 124, 142, 134 can be wrapped about the coupling sleeve 200. Adhesive can cure to affix the rectangular segments 124, 142, 134 and connecting segments 146, 148 to the sleeve 200 as illustrated in FIGS. 9 and 10.

FIG. 11 is a pictorial system 10 for evaluating electrical activity and performing ablative procedures on a heart 12 of a living subject. The treatment illustrated represents an example of an application where the spring assembly 100 can be used as an intravascular force probe.

The system 10 illustrated in FIG. 11 includes a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Areas determined to be abnormal, for example by evaluation of electrical activation maps of the heart, can be ablated by application of thermal energy, e.g., by passage of radiofrequency electrical current through wires in the catheter to one or more electrodes at the distal tip 18, which apply the radiofrequency energy to target tissue. The energy is absorbed in the tissue, heating it to a point (typically above 50° C.) at which point it permanently loses its electrical excitability. This procedure creates non-conducting lesions in the cardiac tissue, which disrupt the abnormal electrical pathway causing the arrhythmia. Such principles can be applied to different heart chambers to diagnose and treat many different types of cardiac arrhythmias.

The catheter 14 can include a handle 20, having suitable controls to enable the operator 16 to steer, position and orient the distal end of the catheter as desired for the ablation. To aid the operator 16, distal portion 18 of catheter 14, or portions proximate thereto, contain the spring assembly 100 which acts as a force sensor to provide feedback to the operator as to force of contact (e.g. force vector) between the distal portion 18 and tissue. The catheter 14 can also contains position sensors, e.g., traces or coils (discussed below), that provide signals to a processor 22, located in a console 24 to provide feedback as to the position of the distal portion 18 in relation to internal anatomy of the patient.

Ablation energy and electrical signals can be conveyed to and from the heart 12 through one or more ablation electrodes 32 located at or near the distal tip 18 via cable 38 to the console 24. Pacing signals and other control signals may be conveyed from the console 24 through the cable 38 and the electrodes 32 to the heart 12.

Wire connections 35 link the console 24 with body surface electrodes 30 and other components of a positioning sub-system for measuring location and orientation coordinates of the catheter 14. The processor 22 or another processor may be an element of the positioning subsystem. The electrodes 32 and the body surface electrodes 30 may be used to measure tissue impedance at the ablation site as taught in U.S. Pat. No. 7,536,218, issued to Govari et al., which is hereby incorporated by reference in its entirety into this application as if set forth in full and attached in the appendix to priority U.S. application 62/943,572. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using a known ablation technique, e.g., radiofrequency energy, ultrasound energy, cryogenic energy, and laser-produced light energy. Such methods are disclosed in commonly assigned U.S. Pat. Nos. 6,814,733, 6,997,924, and 7,156,816, which are hereby incorporated by reference in their entirety into this application as if set forth in full and attached in the appendix to priority U.S. application 62/943,572.

The positioning subsystem may also include a magnetic position tracking arrangement that determines the position and orientation of the catheter 14 by generating magnetic fields in a predefined working volume and sensing these fields at the catheter, using coils or traces disposed within the catheter, typically proximate to the tip. A positioning subsystem is described in U.S. Pat. No. 7,756,576, which is hereby incorporated by reference in its entirety into this application as if set forth in full and attached in the appendix to priority U.S. application 62/943,572, and in the above-noted U.S. Pat. No. 7,536,218.

Operator 16 may observe and regulate the functions of the catheter 14 via console 24. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing coils or traces located distally in the catheter 14. The digitized signals are received and used by the console 24 and the positioning system to compute the position and orientation of the catheter 14, and to analyze the electrical signals from the electrodes and the contact force sensors.

The console 24 can include an electrical diagnostic system including a processor and a memory in communication with the processor with instructions thereon that when executed by the processor cause the processor to receive a first electrical signal corresponding to a first distance between a first pair of inductive coils 184, 116 in the spring assembly 100, receive a second electrical signal corresponding to a second distance between a second pair of inductive coils 184, 118 in the spring assembly 100, receive a third electrical signal corresponding to a third distance between a third pair of inductive coils 184, 120 in the spring assembly, and determine a three dimensional force vector representing a force applied to the atraumatic distal end of the catheter 14, the force vector determined based in at least in part on the first electrical signal, the second electrical signal, and the third electrical signal.

The subject matter disclosed herein concerns structures including the spring assembly 100 within the catheter 14 that may be used to provide feedback to a user of an ablation catheter (e.g., electrophysiologist), the feedback concerning the force exerted on the catheter's tip and any electrodes disposed thereon. The feedback can further include catheter location. These structures reside within the small inner diameter of the catheter (e.g., often equal to or less than about 0.1 inch) yet overcome various design constraints related thereto to provide the feedback reliably. For example, metal coils may be used to detect location within a magnetic field and/or relative position in relation to another coil. Generally, larger and thicker coils with more turns are easier to detect than smaller and thinner coils with fewer turns and the size of the coils is limited by the interior geometry of the catheter 14. Further, when such coils are fabricated as traces on a circuit board or flexible circuit via a lithographic process, the process limits the trace pitch. Although the option is available to increase thickness of the circuit by additional layers lithographically, this option has two disadvantages. First, it is expensive because fabrication costs are proportional to the number of layers. That is, other things being equal, a flexible circuit having more layers costs more to fabricate than one having fewer layers. Second, non-linearity of yield is also proportional to the number of layers. That is, the yield from the coils is compromised because non-linearity of the yield increases with the number of traces. These design challenges are compounded by inclusion of additional structures proximate to the location traces including the bendable coupler 190 and irrigation structure. Further, cross-talk interference that may arise from packing the structures in a tight space should be accounted for. So too should the need for ease of assembly and wiring for safe products and positive patient outcomes.

The descriptions contained herein are examples of embodiments of the invention and are not intended in any way to limit the scope of the invention. As described herein, the invention contemplates many variations and modifications of a catheter, spring assembly, and force probe including alternative materials for component parts, alternative geometrical configurations, alternative methods of construction, and alternative methods of use. Modifications and variations apparent to those having ordinary skill in the art according to the teachings of this disclosure are intended to be within the scope of the claims which follow.

What is claimed is:

1. A spring assembly comprising:
   a tubular body extending along a longitudinal axis, the tubular body sized to traverse vasculature;
   a first mounting surface comprising T-shaped indentations thereon and a first arcuate length partially circumscribing the longitudinal axis and configured to directly couple to a portion of a first electrical circuit, the first mounting surface positioned in the tubular body, perpendicular to the longitudinal axis over a majority of the first arcuate length, and facing a first direction parallel to the longitudinal axis;
   a second mounting surface comprising T-shaped indentations thereon and a second arcuate length partially circumscribing the longitudinal axis and configured to directly couple to a portion of a second electrical circuit, the second mounting surface positioned in the tubular body, perpendicular to the longitudinal axis over a majority of the second arcuate length, and facing toward the first mounting surface in a second direction opposite the first direction; and
   a compressible framework extending between the first mounting surface and the second mounting surface.

2. The spring assembly of claim 1, further comprising:
   a first opening in the tubular body, the first opening circumscribed by the first mounting surface and the compressible framework; and
   a second opening in the tubular body, the second opening circumscribed by the second mounting surface and the compressible framework.

3. The spring assembly of claim 2, the first and second openings being at least partially collapsible in response to compression of the compressible framework.

4. The spring assembly of claim 1, further comprising:
   a plurality of openings circumscribed at least in part by the compressible framework and being at least partially collapsible in response to compression of the compressible framework.

5. The spring assembly of claim 4,
   wherein a first opening of the plurality of openings is circumscribed in part by the first mounting surface, and
   wherein a second opening of the plurality of openings is circumscribed in part by the second mounting surface.

6. The spring assembly of claim 1, further comprising:
   a plurality of first mounting surfaces comprising said first mounting surface;
   a plurality of second mounting surfaces comprising said second mounting surface;
   the first electrical circuit; and
   the second electrical circuit,
      wherein the first electrical circuit is engaged to the plurality of first mounting surfaces, and
      wherein the second electrical circuit is engaged to the plurality of second mounting surfaces.

7. The spring assembly of claim 6,
   wherein each mounting surface of the plurality of first mounting surfaces and the plurality of second mounting surfaces each comprise substantially similar dimensions to each other,
   wherein the plurality of first mounting surfaces comprises three mounting surfaces spaced 120° from each other as measured rotationally about the longitudinal axis,
   wherein the three mounting surfaces of the plurality of first mounting surfaces comprise the first mounting surface,
   wherein the plurality of second mounting surfaces comprises another three mounting surfaces spaced 120° from each other as measured rotationally about the longitudinal axis, and
   wherein the three mounting surfaces of the plurality of second mounting surfaces comprises the second mounting surfaces.

8. The spring assembly of claim 1, further comprising:
   a first plurality of engagement extensions extending in the first direction from a first end of the tubular body, each of the first plurality of engagement extensions comprising a protrusion extending therefrom in a circumferential direction about the longitudinal axis; and
   a second plurality of engagement extensions extending in the second direction from a second end of the tubular body, each of the second plurality of engagement extensions comprising a protrusion extending therefrom in a circumferential direction about the longitudinal axis.

9. The spring assembly of claim 8,
the first plurality of engagement extensions consisting of three protrusions, and
the second plurality of engagement extensions consisting of three protrusions.

10. The spring assembly of claim 1, further comprising:
the first electrical circuit affixed to the first mounting surface, the first electrical circuit comprising a first inductive coil; and
the second electrical circuit affixed to the second mounting surface, the second electrical circuit comprising a second inductive coil.

11. The spring assembly of claim 1, further comprising:
the first electrical circuit; and
the second electrical circuit,
wherein the first electrical circuit comprises three planar inductive coils coplanar to each other in a first plane orthogonal to the longitudinal axis, and
wherein the second electrical circuit comprises another three planar inductive coils coplanar to each other in a second plane orthogonal to the longitudinal axis and spaced apart from the first plane.

12. An intravascular force probe comprising:
a proximal tube;
an atraumatic distal end, the proximal tube and atraumatic distal end defining a longitudinal axis along which the force probe extends;
a first inductive coil comprising a first acuate length partially circumscribing the longitudinal axis and affixed between the proximal tube and the atraumatic distal end such that the first inductive coil is confined in a first plane perpendicular to the longitudinal axis;
a second inductive coil comprising a second acuate length partially circumscribing the longitudinal axis and affixed between the proximal tube and the atraumatic distal end such that the second inductive coil is confined in a second plane perpendicular to the longitudinal axis;
a catheter coupler affixed to the proximal tube and the atraumatic distal end and structurally supporting the first inductive coil and the second inductive coil, the catheter coupler comprising a compressible framework compressible parallel to the longitudinal axis to move the first inductive coil and the second inductive coil toward each other; and
a first connecting conductor electrically connecting the first inductive coil, the first connecting conductor extending circumferentially about the longitudinal axis within the first plane and positioned outside an outer surface of the catheter coupler.

13. The intravascular force probe of claim 12, further comprising:
a third inductive coil confined in the first plane;
a fourth inductive coil confined in the second plane;
a fifth inductive coil confined in the first plane; and
a sixth inductive coil confined in the second plane.

14. The intravascular force probe of claim 13, further comprising:
an electrical diagnostic system configured to:
receive a first electrical signal corresponding to a first distance between the first inductive coil and the second inductive coil;
receive a second electrical signal corresponding to a second distance between the third inductive coil and the fourth inductive coil;
receive a third electrical signal corresponding to a third distance between the fifth inductive coil and the sixth inductive coil; and
determine a three dimensional force vector representing a force applied to the atraumatic distal end, the force vector determined based at least in part on the first electrical signal, the second electrical signal, and the third electrical signal.

15. The intravascular force probe of claim 12,
the compressible framework further bendable to define a bend in the longitudinal axis, thereby causing the first plane and the second plane to be non-parallel.

16. The intravascular force probe of claim 12, further comprising:
a generator electrically connected to the first inductive coil; and
an electrical measurement tool electrically connected to the second inductive coil.

17. A catheter comprising:
a proximal tube;
an atraumatic distal end, the proximal tube and atraumatic distal end defining a longitudinal axis;
a first inductive coil comprising a first acuate length partially circumscribing the longitudinal axis and affixed between the proximal tube and the atraumatic distal end and confined in a first plane perpendicular to the longitudinal axis;
a second inductive coil comprising a first acuate length partially circumscribing the longitudinal axis and affixed between the proximal tube and the atraumatic distal end and confined in a second plane perpendicular to the longitudinal axis; and
a compressible framework compressible parallel to the longitudinal axis to move the first inductive coil and the second inductive coil toward each other;
a catheter coupler affixed to the proximal tube and the atraumatic distal end, the catheter coupler comprising the compressible framework and structurally supporting the first inductive coil and the second inductive coil;
a first connecting conductor electrically connecting the first inductive coil, the first connecting conductor extending circumferentially about the longitudinal axis within the first plane and positioned outside an outer surface of the catheter coupler; and
an elongated catheter tube affixed to the proximal tube, surrounding the first inductive coil, surrounding the second inductive coil, surrounding the compressible framework, surrounding the catheter coupler, and extending to a proximal end of the catheter.

\* \* \* \* \*